(12) United States Patent
Bakeman

(10) Patent No.: US 10,080,637 B2
(45) Date of Patent: Sep. 25, 2018

(54) TOOTH DISPLAY MEASUREMENT DEVICE

(71) Applicant: Elizabeth Mary Bakeman, Grand Rapids, MI (US)

(72) Inventor: Elizabeth Mary Bakeman, Grand Rapids, MI (US)

(*) Notice: Subject to any disclaimer, the term of this patent is extended or adjusted under 35 U.S.C. 154(b) by 17 days.

(21) Appl. No.: 15/490,399

(22) Filed: Apr. 18, 2017

(65) Prior Publication Data
US 2017/0296315 A1    Oct. 19, 2017

Related U.S. Application Data

(60) Provisional application No. 62/324,637, filed on Apr. 19, 2016.

(51) Int. Cl.
*A61C 19/04* (2006.01)
*A61B 5/107* (2006.01)
*A61B 5/00* (2006.01)

(52) U.S. Cl.
CPC ............ *A61C 19/04* (2013.01); *A61B 5/1072* (2013.01); *A61B 5/4547* (2013.01)

(58) Field of Classification Search
CPC ....... A61C 19/04; A61C 1/084; A61C 19/043; A61C 19/046; A61B 5/1075; A61B 5/4547
USPC ...................................................... 433/3, 72
See application file for complete search history.

(56) References Cited

U.S. PATENT DOCUMENTS

| | | | | |
|---|---|---|---|---|
| 4,762,491 A * | 8/1988 | Bolton | .................. | A61C 19/04 33/514 |
| 5,226,428 A * | 7/1993 | Lee | ........................ | A61C 19/04 33/514 |
| 5,971,756 A * | 10/1999 | Fjelstad | ................. | A61C 19/04 433/68 |
| 6,783,359 B2 * | 8/2004 | Kapit | ..................... | A61C 7/146 433/141 |
| 7,254,898 B1 * | 8/2007 | Armstrong | .............. | B43L 7/007 33/419 |
| 9,662,193 B1 * | 5/2017 | Saiz | ........................ | A61C 19/05 |
| 2005/0033315 A1 * | 2/2005 | Hankins | ................. | A61B 90/11 606/129 |
| 2005/0255421 A1 * | 11/2005 | Michaelson | ............. | A61C 3/10 433/4 |
| 2006/0057533 A1 * | 3/2006 | McGann | .................. | A61C 7/12 433/25 |
| 2008/0145811 A1 * | 6/2008 | Diers | .................... | A61B 5/1072 433/3 |
| 2008/0241784 A1 * | 10/2008 | Chung | .................... | A61C 1/084 433/76 |
| 2009/0320307 A1 * | 12/2009 | Richter | .................. | G01B 3/205 33/512 |

(Continued)

*Primary Examiner* — Nicholas Lucchesi
(74) *Attorney, Agent, or Firm* — Warner Norcross + Judd LLP

(57) ABSTRACT

A tooth display measurement device includes a measurement portion, an inner surface and an outer surface. A tooth rest platform projects outwardly from the inner surface. The tooth rest platform is spaced between the upper end and the lower end, and ruler markings are printed or otherwise affixed on the outer surface. A a handle projects from the lower end of the measurement portion. The device assists in an accurate reading of tooth display as the measurement portion is inserted between the lip and the teeth of the user with the tooth rest platform abutting the biting edge of the tooth to be measured.

18 Claims, 1 Drawing Sheet

(56) References Cited

U.S. PATENT DOCUMENTS

2012/0076268 A1* 3/2012 Archibald ................ A61B 6/04
378/62
2013/0288196 A1* 10/2013 Gordon .................... A61C 1/12
433/93

* cited by examiner

TOOTH DISPLAY MEASUREMENT DEVICE

BACKGROUND OF THE INVENTION

The present invention relates to the measurement of a visible amount of a user's tooth, commonly referred to in the art as "tooth display." In particular, the present invention relates to a device that easily captures an accurate reading of tooth display with the lips at rest and in a full smile.

Dentists, orthodontists and other tooth care professionals desire for accurate measurement of the amount of tooth display on a patient. In practice, these professionals typically use standard style rules or probes to measure tooth display by holding them in front of the user's mouth, to measure the amount of visible tooth (i.e., the amount of an upper tooth extending below the user's upper lip, or in some cases the amount of a user's lower tooth extending above the bottom lip). Problems arise in that rulers are too thick so they distort the lip and create inaccuracies. Additionally, tooth display that is under the lip is difficult to measure with traditional measuring devices.

SUMMARY OF THE INVENTION

The present invention provides a tooth display measurement device with a tooth rest seat or platform to rest against the biting edge of each tooth that will be measured giving an accurate result of the tooth display.

In one embodiment, the tooth display measurement device includes a measurement portion including a thin strip of material having an outer surface, an inner surface opposite the outer surface, an upper end, and a lower end opposite the upper end. The tooth rest platform projects outwardly from the inner surface. The tooth rest platform is spaced between the upper end and the lower end. Ruler markings are printed or otherwise affixed on the outer surface, and a handle projects from the lower end of the measurement portion.

In another embodiment, a ruler support extends between the lower end and the handle, the ruler support extends at an angle from the outer surface of the lower end, and the handle extends at an angle from the ruler support. The ruler support introduces a predetermined lateral spacing between the measurement portion and the handle, for example, to account for the width of the user's lips and create a more accurate measurement and more comfortable user experience.

In another embodiment, at least a portion of the measurement portion is curved in a direction away from said handle. For example, the inner surface of the measurement portion may be slightly concave to match the shape of a user's teeth and gums and provide an added degree of comfort and also increase the accuracy of measurements.

In one embodiment, the positioning of the tooth rest platform is predetermined to generally match the proportions of a user's mouth. The tooth rest portion may be positioned closer to the lower end than the upper end of the measurement portion. The tooth rest platform may extend perpendicular to the inner surface of the measurement portion. In another embodiment, the measurement portion has a thickness that is narrower than that of the handle.

In another embodiment, the present invention provides a tooth display measurement device system for measuring an amount of a user's tooth that is visible. The system includes a handle gripped by the user, a support portion extending at an angle from the handle; and a measurement portion extending at an angle from the support portion in a direction away from the handle, at least part of said measurement portion extending between the teeth and lip of the user. The measurement portion includes an outer surface having ruler markings printed thereon and an inner surface including a tooth rest platform projecting outwardly therefrom and positioned against the bite surface of a tooth of the user to be measured. The tooth rest platform is positioned between the upper and lower ends of the measurement portion.

As stated above, the present invention easily captures an accurate reading of tooth display with the lips at rest and in a full smile. It is thin, so it easily slides under the lip and does not distort the lip and rests against the biting edge of the teeth so that it is stable and accurate. The claimed invention differs from the rulers or probes that currently exist. These rulers and probes are not stable and are therefore inaccurate. Rulers and probed are designed for other purposes and are not specifically designs to measure tooth display. The present device would be made with a rest seat to rest against the biting edge of each tooth that will be measured giving a very accurate result. In particular, the version of the device described herein includes: 1. a ruler/measuring component, 2. a tooth rest, and 3. a handle. The tooth rest is placed against the teeth, the ruler is used to measure tooth display and the handle allows the instrument to be held by the clinician or dental professional. A key element of the device is the tooth rest. It must be narrow enough to rest on an individual tooth but have enough bulk to be stable. The invention may be a disposable measuring device made of plastic. The toot rest is positioned at "0" measurement, with 1 mm increments for measuring both above and below the "0" mark. There may be a slight curve to the upper portion of the ruler to slide under the lip. The markings may be color coded for ease of reading small the small measurements.

These and other objects, advantages, and features of the invention will be more fully understood and appreciated by reference to the description of the current embodiments and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and may be practiced or may be carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE CURRENT EMBODIMENT

Figures 1, 2:
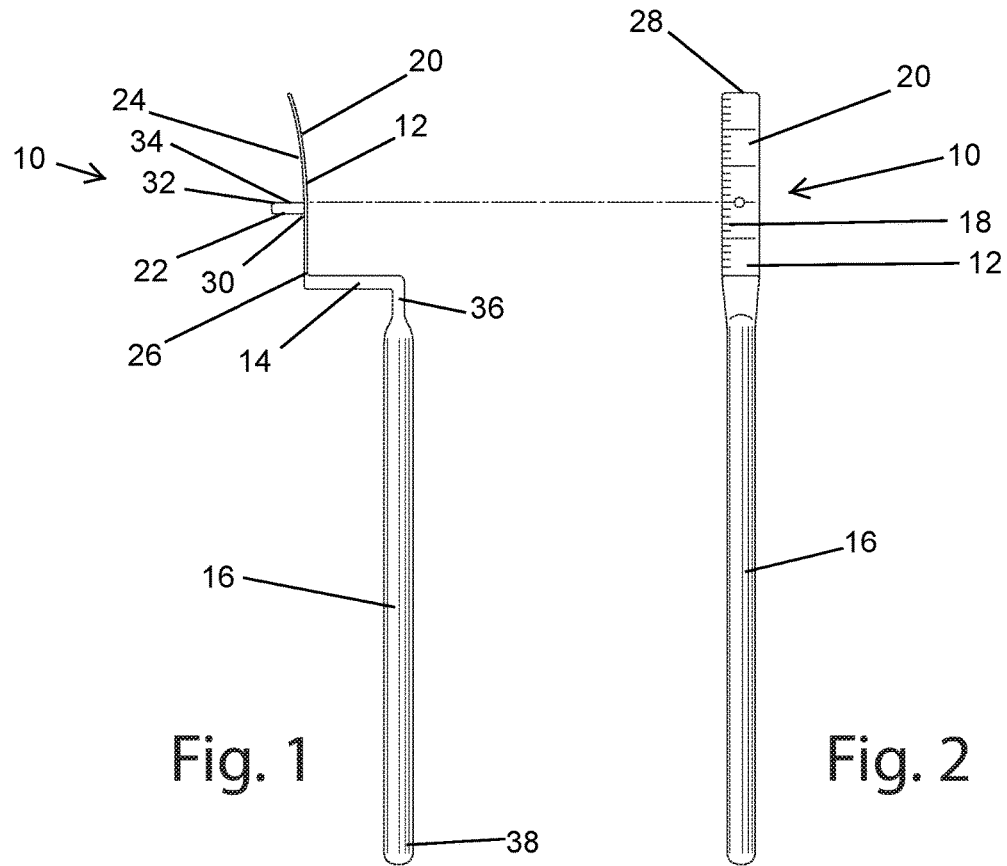
FIG. 1 is a side profile view according to one embodiment of the present invention.
FIG. 2 is a front view thereof.
Figure 3:
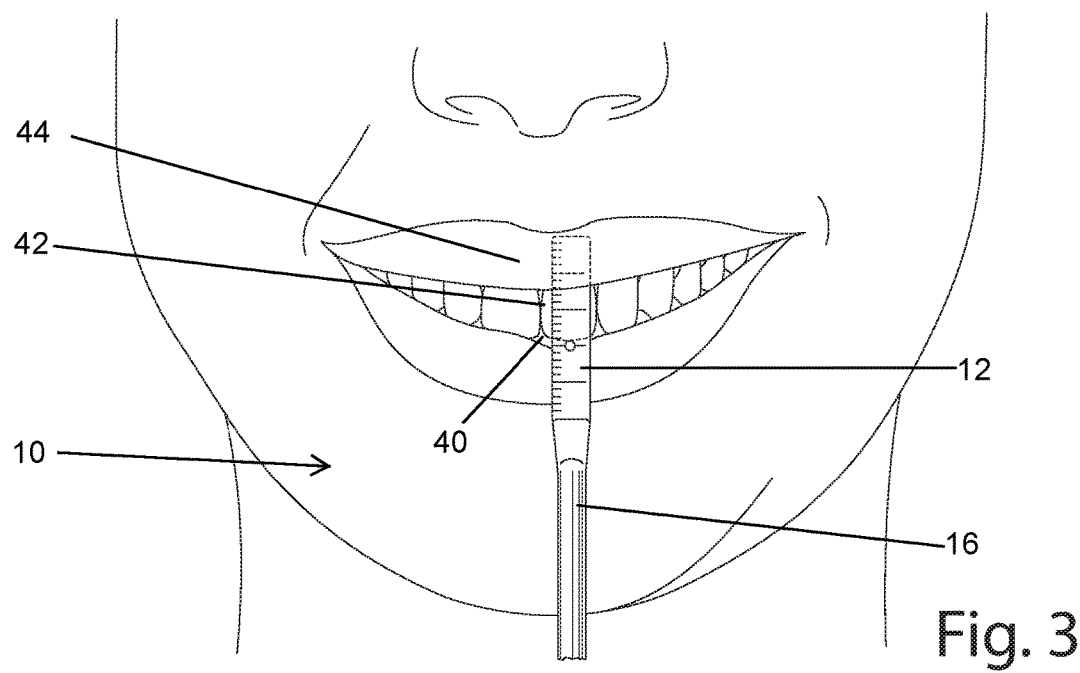
FIG. 3 is a front view thereof showing the device in use.

A tooth display measurement device that easily captures an accurate reading of tooth display with the lips at rest and in a full smile is shown in FIGS. 1-3 and generally designated 10. In one embodiment, the device includes a measurement portion 12, a support portion 14 and a handle 16. The measurement portion 12 has ruler markings 18 printed on an outer surface 20 and a tooth rest platform 22 extending from an inner surface 24. The support portion 14 extends at an angle from the measurement portion 12 and the handle 16 extends downwardly from the support portion 14. The device 10 is designed to take an accurate reading of tooth display by inserting the measurement portion 12 between the lip and the teeth of the user with the tooth rest platform 22 abutting the tip 40 of the tooth 42 to be measured.

Structure

As illustrated, the tooth display measurement device 10 may be formed from a variety of materials, such as plastic or steel. It may be formed as a single unitary piece, such as a single molded plastic piece or bent steel, or it may be a multi-component piece, such as a plastic measurement portion 12 attached to a metal support portion 14 and/or handle 16.

The measurement portion 12, as noted above, is designed to be inserted between the lip 44 and the teeth 42 of a user with the inner surface 24 facing and resting against the surface of the tooth to be measured. The measurement portion 12 is formed from a thin strip of material, such as from one of the materials noted above. Due to the importance of (1) taking an accurate measurement and (2) providing a comfortable experience to the user, the size and shape of the measurement portion 12 is carefully predetermined. In one embodiment, the width of the measurement portion is relatively narrow, such as approximately 5 mm. As illustrated, the measurement portion includes a lower end 26 forming a base for the measurement portion 12 and an upper end 28 forming the tip of the device 10. The overall length of the measurement portion 12 is defined between the upper end 28 and lower end 26. Based on the above noted factors of comfort and accuracy, the length of the measurement portion 12 is important. In one embodiment, the length of the measurement portion 12 is between about 15 mm and about 30 mm. In the illustrated embodiment, the length of the measurement portion is 25 mm. As also shown in the illustrated embodiment, at least part of the measurement portion 12 may be provided with a curved shape. Referring to FIG. 1, the inner surface 24 of the measurement portion is curved near the upper end 28 such that the inner surface 24 is concave (i.e., curved in a direction away from the outer surface 20 and away from the handle 16). The curved shape may match the shape of the user's teeth and mouth, enabling the measurement portion to seat flush against the teeth and provide a more accurate measurement. In one embodiment, the measurement portion 12 may have a degree of flexibility to enable it to adapt to a wider variety of mouth shapes and sizes.

The tooth rest platform 22 projects outwardly from the inner surface 24 of the measurement portion 12. In the illustrated embodiment, the tooth rest platform 22 extends generally perpendicular to the inner surface 24. The tooth rest platform 22 includes a base 30 connected to the inner surface 24 and a distal end 32 opposite the base 30. The tooth rest platform 22 defines a length between the base 30 and the distal end 32. So as not to extend too far in to the mouth of the user, the length of the tooth rest platform 22 is generally shorter than the length of the measurement portion 12. The positioning of the tooth rest platform 22 along the length of the measurement portion 12 is also important for both accuracy of measurement and user comfort, as it sets the distance between the tooth rest platform 22 and the upper end 28 of the measurement portion 12—referred to as the upper measurement length. This upper measurement length is the amount the measurement portion 12 can extend upwardly between the user's lip and teeth/gums. If the upper measurement length is too great, the upper end 28 of the measurement portion would uncomfortable engage the inside of the user's lip. In one embodiment, the tooth rest platform 22 is positioned so that the upper measurement length is about 60% of the overall length of the measurement portion 12. More particularly, in the illustrated embodiment, the length of the measurement portion is about 25 mm and the length of the upper measurement portion is about 15 mm, such that the tooth rest platform 22 is positioned about 15 mm from the upper end 28. The distance between the tooth rest platform 22 and the lower end 26 is therefore about 10 mm (or slightly less when accounting for the thickness of the tooth rest platform 22).

As illustrated, the outer surface 20 of the measurement portion includes ruler markings 18 printed or otherwise disposed thereon. The markings 18 are generally scaled in millimeters, and may extend from the lower end (or "base") 26 of the measurement portion 12 to the upper end 28. In the illustrated embodiment, however, the "0" line of the ruler markings is aligned with the upper side 34 of the tooth rest platform 22, such that a distance above the platform 22 can be accurately measured as well as a distance below the platform 22. The tooth rest platform 22 may be formed with the measurement portion 12 as a single piece or may be a separate piece otherwise conventionally attached to the measurement portion 12.

The support portion 14 extends at an angle from the measurement portion 12. More specifically, in the illustrated embodiment, the support portion 14 extends from the base 26 of the measurement portion 12 generally perpendicular to the measurement portion 12. In one embodiment, the support portion 14 laterally offsets the measurement portion 12 from the handle 16, and generally extends a length sufficiently greater than the width of a user's lip to enable the handle to be clear of the lip 44 and thus provide a degree of comfort for the user. The length of the support portion 14 may vary from application to application, but in the illustrated embodiment the support portion has a length or about 10 mm.

The handle 16 extends at an angle from the support portion 14 (or, in another embodiment not including a support portion, at an angle or curve from the measurement portion). In general, the handle 16 is thicker and more rigid than the measurement portion 12 to provide a stable grip body for the device 10. In the illustrated embodiment, the handle 16 has an upper end 36 adjacent the support portion 14 and a lower end 38 and the handle 16 has a length between theses ends of about 12 cm.

Operation

Referring to FIGS. 1-3, operation of the device 10 is generally performed by a dental professional. As an initial step, the dental professional grips the handle 16 in his/her hand and inserts the measurement portion 12 into a user's mouth between the teeth and the lip of the user. The user determines a particular tooth 42 for measurement of the tooth display (i.e., the amount of that tooth extending below or above the user's lip. If the chosen tooth 42 is on the bottom, then the professional inserts the measurement portion 12 between the bottom teeth and bottom lip of the user, and if the chosen tooth is on the top, the professional inserts the measurement portion 12, starting with the upper end 28, between the upper teeth and the upper lip of the user.

The dental professional guides the device 10 until the upper surface 34 of the tooth rest platform 22 abuts the biting edge or tip 40 of the particular tooth 42 to be measured and the inner surface 24 of the measurement portion lies against the front surface of the tooth to be measured. With the device 10 in this position, the dental professional may instruct the user to smile, or to keep the lips in the resting position, depending on the type of measurement to be taken. Once the user's lip is in the chosen position, the dental professional reads and records the amount of tooth display, namely, the distance between the "0" reading on the measurement portion and the edge of the user's lip.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Features of various embodiments may be used in combination with features from other embodiments. Directional terms, such as "vertical," "horizontal," "top," "bottom," "front," "rear," "upper," "lower," "inner," "inwardly," "outer," "outwardly," "forward," and "rearward" are used to assist in describing the invention based on the orientation of the embodiments shown in the illustrations. The use of directional terms should not be interpreted to limit the invention to any specific orientation(s). Any reference to claim elements in the singular, for example, using the articles "a," "an," "the" or "said," is not to be construed as limiting the element to the singular.

The invention claimed is:

1. A tooth display measurement device, comprising:
   a measurement portion including a thin strip of material having an outer surface, an inner surface opposite said outer surface, an upper end and a lower end opposite said upper end;
   a tooth rest platform projecting outwardly from said inner surface, said tooth rest platform spaced between said upper end and said lower end;
   ruler markings on said outer surface; and
   a handle projecting from said lower end of said measurement portion, wherein said measurement portion is laterally offset from said handle by a support portion.

2. The device of claim 1 including a ruler support between said lower end and said handle, said ruler support extending at an angle from said outer surface of said lower end, said handle extending at an angle from said ruler support.

3. The device of claim 2 wherein at least a portion of said measurement portion is curved in a direction away from said handle.

4. The device of claim 3 wherein said tooth rest platform is positioned closer to said lower end than said upper end.

5. The device of claim 4 wherein said tooth rest platform extends perpendicular to said inner surface of said measurement portion.

6. The device of claim 5 wherein said measurement portion defines a length between said upper end and said lower end, and wherein said length is between about 15 mm and about 30 mm.

7. The device of claim 6 wherein said length is about 25 mm.

8. The device of claim 7 wherein said measurement portion defines an upper measurement length between said tooth rest platform and said upper end of said measurement portion, and wherein said upper measurement length is between about 10 mm and about 20 mm.

9. The device of claim 8 wherein said upper measurement length is about 15 mm.

10. The device of claim 6 wherein said upper measurement length is about 60% of the length of the measurement portion.

11. The device of claim 10 wherein said measurement portion has a first thickness and said handle has a second thickness greater than said first thickness.

12. A tooth display measurement device, comprising:
    a handle having a first end and a second end opposite said first end;
    a support portion extending at an angle from said handle; and
    a measurement portion extending at an angle from said support portion in a direction away from said handle with the measurement portion laterally offset from the handle, said measurement portion including:
      a lower end connected to said support portion;
      an upper end opposite said lower end and defining a length of said measurement portion between said upper and lower ends;
      an outer surface having ruler markings printed thereon along said length of said measurement portion; and
      an inner surface opposite said outer surface, said inner surface including a tooth rest platform projecting outwardly therefrom, said tooth rest platform positioned between said upper and lower ends of said measurement portion.

13. The device of claim 12 wherein at least a portion of said inner surface of said measurement portion is concave.

14. The device of claim 13 wherein said measurement portion includes an upper measurement length defined between said tooth rest platform and said upper end, wherein said upper measurement length is about 60% of the length of the measurement portion.

15. The device of claim 14 wherein said upper measurement length is about 10 mm.

16. The device of claim 15 wherein said tooth rest platform extends perpendicular to said inner surface, said tooth rest platform including a distal end and defining a length between said inner surface and said distal end, said length of said tooth rest platform shorter than said length of said upper measurement portion.

17. The device of claim 16 wherein said support portion is perpendicular to said handle and at least a portion of said measurement portion.

18. A tooth display measurement device system for measuring an amount of a user's tooth that is visible comprising:
- a handle adapted to be gripped by the user, said handle having a first end and a second end opposite said first end;
- a support portion including a first end and a second end, said first end extending at an angle from said handle; and
- a measurement portion extending at an angle from said second end of said support portion in a direction away from said handle, at least part of said measurement portion configured to extend between the teeth and lip of the user, said measurement portion including:
  - a lower end connected to said support portion;
  - an upper end opposite said lower end and defining a length of said measurement portion between said upper and lower ends;
  - an outer surface having ruler markings printed thereon along said length of said measurement portion; and
  - an inner surface opposite said outer surface, said inner surface including a tooth rest platform projecting outwardly therefrom and adapted to be positioned against the bite surface of a tooth of the user to be measured, said tooth rest platform positioned between said upper and lower ends of said measurement portion.

* * * * *